US00PP35719P2

(12) United States Plant Patent
Heuger

(10) Patent No.: US PP35,719 P2
(45) Date of Patent: Apr. 2, 2024

(54) ***SAXIFRAGA* PLANT NAMED 'SH 1934'**

(50) Latin Name: *Saxifraga cortusifolia*
Varietal Denomination: SH 1934

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/216,579

(22) Filed: Jun. 29, 2023

Related U.S. Application Data

(60) Provisional application No. 63/441,450, filed on Jan. 27, 2023.

(51) Int. Cl.
*A01H 5/02* (2018.01)
*A01H 6/80* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — C. Anne Whealy

(57) ABSTRACT

A new and distinct cultivar of *Saxifraga* plant named 'SH 1934', characterized by its broadly upright and mounded plant habit; moderately vigorous to vigorous growth habit and moderate growth rate; leaves with dark green-colored upper surfaces and dark red-colored lower surfaces; freely flowering habit; and purplish red-colored flowers that are held above the foliar plane.

2 Drawing Sheets

Figure 1:
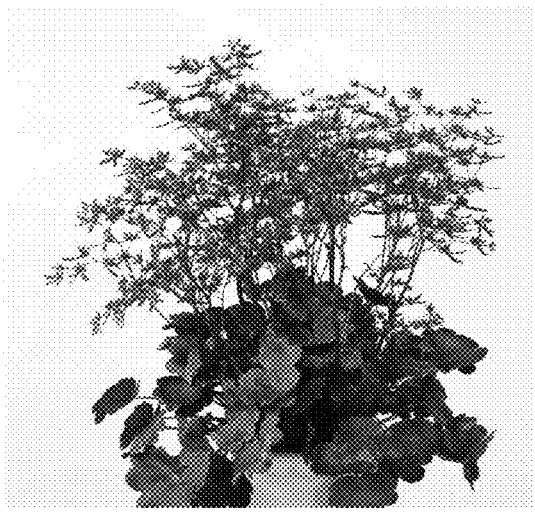

Botanical designation: *Saxifraga cortusifolia.*
Cultivar denomination: 'SH 1934'.

An European Community Plant Breeder's Rights application for the instant plant was filed by the Inventor/Applicant, Mr. Josef Heuger of Glandorf, Germany, on Jul. 12, 2022, application number 2022/1715. Foreign priority is not claimed to this application.

BACKGROUND OF THE INVENTION

The present invention relates to a new and distinct cultivar of *Saxifraga* plant, botanically known as *Saxifraga cortusifolia* and hereinafter referred to by the name 'SH 1934'.

The new *Saxifraga* plant is a product of a planned breeding program conducted by the Inventor in Glandorf, Germany. The objective of the breeding program was to create new uniform and strong *Saxifraga* plants with unique and attractive plant habit, leaf and flower coloration.

The new *Saxifraga* plant originated from a cross-pollination conducted by the Inventor in Glandorf, Germany in October, 2017 of a proprietary selection of *Saxifraga cortusifolia* identified as code number 17-843, not patented, as the female, or seed patent and a proprietary selection of *Saxifraga cortusifolia* identified as code number 16-087, not patented, as the male, or pollen parent. The new *Saxifraga* plant was discovered and selected by the Inventor as a single flowering plant from within the progeny of the stated cross-pollination grown in a controlled greenhouse environment in Glandorf, Germany in September, 2018.

Asexual reproduction of the new *Saxifraga* plant by in vitro axillary meristem culture in a controlled environment in Glandorf, Germany since May, 2019 has shown that the unique features of this new *Saxifraga* plant are stable and reproduced true to type in successive generations.

SUMMARY OF THE INVENTION

Plants of the new *Saxifraga* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SH 1934'. These characteristics in combination distinguish 'SH 1934' as a new and distinct *Saxifraga* plant:

1. Broadly upright and mounded plant habit.
2. Moderately vigorous to vigorous growth habit and moderate growth rate.
3. Leaves with dark green-colored upper surfaces and dark red-colored lower surfaces.
4. Freely flowering habit.
5. Purplish red-colored flowers that are held above the foliar plane.

Plants of the new *Saxifraga* differ primarily from plants of the female parent selection in flower color as flowers of plants of the new *Saxifraga* are purplish red in color whereas flowers of plants of the female parent selection are rose pink in color.

Plants of the new *Saxifraga* differ primarily from plants of the male parent selection in the following characteristics:

1. Upper leaf surfaces of plants of the new *Saxifraga* are darker green in color than upper leaf surfaces of plants of the male parent selection.
2. Flowers of plants of the new *Saxifraga* are purplish red in color whereas flowers of plants of the male parent selection are dark red in color.

Plants of the new *Saxifraga* can be compared to plants of *Saxifraga cortusifolia* 'SH 1925', disclosed in U.S. Plant Pat. No. 34,830. Plants of the new *Saxifraga* differ primarily from plants of 'SH 1925' in flower color as flowers of plants of the new *Saxifraga* are purplish red in color whereas flowers of plants of 'SH 1925' are purplish pink and purplish red bi-colored.

BRIEF DESCRIPTION OF THE PHOTOGRAPHS

The accompanying colored photographs illustrate the overall appearance of the new *Saxifraga* plant showing the colors as true as it is reasonably possible to obtain in colored reproductions of this type. Colors in the photographs may differ slightly from the color values cited in the detailed botanical description which accurately describe the colors of the new *Saxifraga* plant.

The photograph at the top of the first sheet (FIG. 1) is a side perspective view of a typical flowering plant of 'SH 1934' grown in a container.

Figure 2:
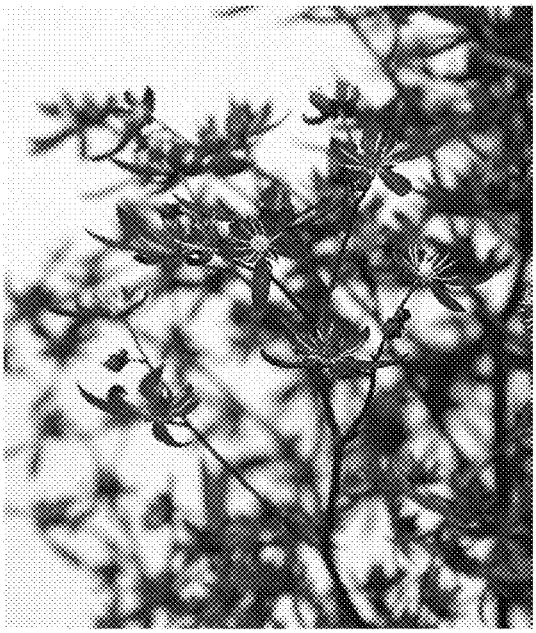

The photograph at the bottom of the first sheet (FIG. 2) is a close-up view of a typical flowering plant of 'SH 1934'.

Figure 3:
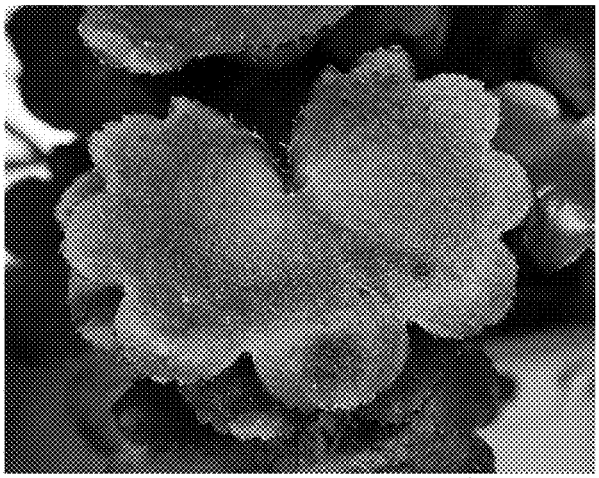

The photograph at the top of the second sheet (FIG. 3) is a close-up view of the upper surface of a typical leaf of 'SH 1934'.

Figure 4:
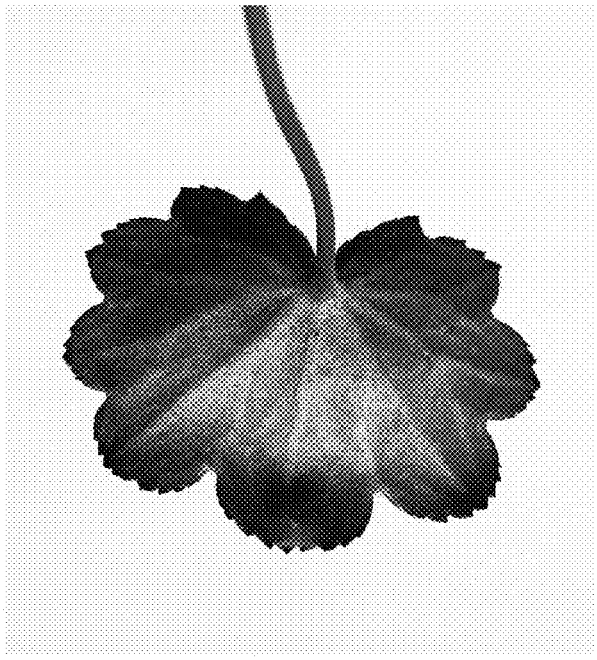

The photograph at the bottom of the second sheet (FIG. 4) is a close-up view of the lower surface of a typical leaf of 'SH 1934'.

DETAILED BOTANICAL DESCRIPTION

The aforementioned photographs and following observations, measurements and values describe plants grown during the late autumn in 12-cm containers in a glass-covered greenhouse in Glandorf, Germany and under cultural practices typical of commercial *Saxifraga* production. During the production of the plants, day temperatures ranged from 18 C to 28 C and night temperatures ranged from 14 C to 20 C. Plants were six months old when the photographs and the description were taken. In the following description, color references are made to The Royal Horticultural Society Colour Chart, 2015 Edition, except where general terms of ordinary dictionary significance are used.

Botanical classification: *Saxifraga cortusifolia* 'SH 1934'.

Parentage:

- *Female, or seed, parent*.—Proprietary selection of *Saxifraga cortusifolia* disclosed as code number 17-843, not patented.
- *Male, or pollen, parent*.—Proprietary selection of *Saxifraga cortusifolia* disclosed as code number 16-087, not patented.

Propagation:

- *Type*.—In vitro axillary meristem culture.
- *Time to initiate roots, winter*.—About 55 days at temperatures about 12 C.
- *Time to produce a rooted young plant, winter*.—About 170 days at temperatures about 4 C to 15 C.
- *Root description*.—Fine to thick, fleshy; typically white to brownish in color; actual color of the roots is dependent on substrate composition, water quality, fertilizer type and formulation, substrate temperature and physiological age of roots.
- *Rooting habit*.—Low amount of branching; sparse.

Plant description:

- *Plant and growth habit*.—Herbaceous perennial; broadly upright and mounding plant habit with flowers held above the foliar plane; overall plant shape, flattened globular; moderately vigorous to vigorous growth habit and moderate growth rate.
- *Plant height, soil level to top of foliar plane*.—About 13.4 cm.
- *Plant height, soil level to top of floral plane*.—About 29.8 cm.
- *Plant diameter* (*area of spread*).—About 28 cm.

Leaf description:

- *Arrangement*.—Leaves arranged in a basal rosette; alternate and single; about 14 basal rosettes per plant.
- *Length*.—About 5 cm.
- *Width*.—About 7 cm.
- *Shape*.—Reniform in outline; palmately lobed.
- *Apex*.—Broadly acute.
- *Base*.—Truncate to shallowly hastate, lobes free.
- *Margin*.—Shallowly dentate to serrate and palmately lobed with about nine lobes per leaf; sinuses shallow in depth and divergent.
- *Texture and luster, upper surface*.—Sparsely pubescent; not rugose; slightly glossy.
- *Texture and luster, lower surface*.—Sparsely pubescent; not rugose; moderately glossy.
- *Venation pattern*.—Pinnate.
- *Color*.—Developing leaves, upper surface: Slightly darker than 147A; narrow marginal edges, close to 200A. Developing leaves, lower surface: Close to 187B to 187C. Fully developed leaves, upper surface: Slightly darker than a blend of NN137B and 147A; narrow marginal edges, close to 200A; venation, slightly darker than a blend of NN137B and 147A tinged with close to 197A. Fully developed leaves, lower surface: Close to 183B; lobe venation, close to 186B.
- *Petioles*.—Length: About 10.4 cm. Diameter: About 3.5 mm. Strength: Weak. Texture and luster, upper and lower surfaces: Sparsely pubescent; slightly glossy. Color, upper surface: Close to 178A; distally, tinged with close to 152A. Color, lower surface: Close to 148A; distally, close to 148B.
- *Stipules*.—Quantity and arrangement: Two at the base of each petiole. Length: About 1.3 cm. Width: About 6.5 mm. Shape: Reniform with fimbriate apices and margins. Color, upper and lower surfaces: Close to 187C.

Flower description:

- *Flower shape and habit*.—Rotate flowers arranged in terminal compound corymbs; freely flowering habit with about 45 flowers per inflorescence and about 630 flowers developing per plant; flowers face mostly upright to slightly outwardly.
- *Fragrance*.—None detected.
- *Natural flowering season*.—Plants begin flowering about six months after planting; plants flower naturally during the autumn in Germany.
- *Flower longevity on the plant*.—About two weeks; flowers persistent.
- *Flower buds*.—Length: About 2.5 mm. Diameter: About 2.25 mm. Shape: Broadly ovate to close to globular. Texture and luster: Smooth, glabrous; slightly glossy. Color: Immature petals, close to 185B; immature sepals, close to N186C.
- *Inflorescence height* (*including peduncle*).—About 26.9 cm.
- *Inflorescence diameter*.—About 13.3 cm.
- *Flower diameter*.—About 2 cm by 2.1 cm.
- *Flower depth* (*height*).—About 6 mm.
- *Petals*.—Quantity and arrangement: About eight, varying between six and twelve, arranged in a single whorl; upper three or four petals are smaller than lower one or two petals. Length, upper petals: About 6 mm to 9 mm. Length, lower petals: About 15 mm to 18 mm. Width, upper petals: About 3 mm to 4 mm.

Width, lower petals: About 5 mm to 6 mm. Shape, upper petals: Elliptic to ovate. Shape, lower petals: Narrowly elliptic to oblanceolate. Apex, upper petals: Acute. Apex, lower petals: Acute, occasionally cleft. Base, upper and lower petals: Attenuate. Margin, upper and lower petals: Entire; not undulate. Texture and luster, upper and lower petals, upper and lower surfaces: Smooth, glabrous; slightly velvety; matte. Color: When opening, upper petals, upper surface: Close to 61B; apices, close to 59A. When opening, lower petals, upper surface: Close to 60B; apices, close to 59A. When opening, upper and lower petals, lower surface: Close to 60D; apices, close to 59A. Fully opened, upper and lower petals, upper surface: Close to 61B; towards the base, close to 61C; towards the apex, close to 60A; venation, similar to lamina colors; with subsequent development, color becoming closer to a blend of 59B and 187D. Fully opened, upper and lower petals, lower surface: Close to 64D; towards the margins and the apex, close to 60A to 60B; venation, similar to lamina colors; with subsequent development, color becoming closer to 64B.

*Sepals*.—Quantity and arrangement: Five, arranged in a single whorl. Length: About 3 mm. Width: About 1.25 mm. Shape: Ovate. Apex: Obtuse. Base: Broadly cuneate. Margin: Entire. Texture and luster, upper surface: Smooth, glabrous; matte. Texture and luster, lower surface: Smooth, glabrous; moderately glossy. Color: When opening and fully opened, upper surface: Close to 183A to 183B; towards the base, close to 147C. When opening and fully opened, lower surface: Close to 183A.

*Peduncles*.—Length: About 25.5 cm. Diameter: About 3 mm. Aspect: About 20 degrees from vertical; secondary peduncles, about 35 degrees from main peduncle axis. Strength: Moderately weak. Texture and luster: Sparsely pubescent; moderately glossy. Color: Close to 187A to 187B.

*Pedicels*.—Length: About 1.3 cm. Diameter: About 0.5 mm. Aspect: About 30 degrees from peduncle axis. Strength: Moderately strong. Texture and luster: Sparsely pubescent; slightly glossy. Color: Close to 197A to 197B; proximally, tinged with close to 183B to 183C.

*Reproductive organs*.—Stamens: Quantity per flower: About ten. Filament length: About 3.25 mm. Filament color: Close to 155D; becoming close to 186D with subsequent development. Anther shape: Double reniform. Anther size: About 0.5 mm by 0.5 mm. Anther color: Close to 187B. Pollen amount: Scarce. Pollen color: Close to 26C to 26D. Pistils: Quantity per flower: About two. Pistil length: About 3.5 mm. Stigma diameter: About 0.2 mm. Stigma shape: Club-shaped. Stigma color: Close to 157A. Style length: About 3.25 mm. Style color: Close to 145D. Ovary color: Close to 145B. Floral bracts: Quantity per flower: One. Length: About 8 mm. Diameter: About 2 mm. Shape: Narrowly oblong to lanceolate. Apex: Bluntly acute. Base: Broadly cuneate. Margin: Entire. Color, upper and lower surfaces: Close to a blend of N186C and 200A. Seeds and fruits: To date, seed and fruit development have not been observed on plants of the new *Saxifraga*.

Temperature tolerance: Plants of the new *Saxifraga* have been observed to tolerate temperatures ranging from about −7 C to about 35 C and to be suitable for USDA Hardiness Zones 8b through 11.

Pathogen & pest resistance: To date, plants of the new *Saxifraga* have not been observed to be resistant to pathogens and pests common to *Saxifraga* plants.

It is claimed:

1. A new and distinct *Saxifraga* plant named 'SH 1934' as illustrated and described.

* * * * *